United States Patent [19]

Ai et al.

[11] Patent Number: 4,493,644

[45] Date of Patent: Jan. 15, 1985

[54] DEVICE FOR MEASURING AND SCRAPING OPERATIONS IN THE FIELD OF PRESTORATIVE DENTISTRY

[75] Inventors: Minoru Ai; Akira Manabe, both of Tokyo; Yoshimasa Igarashi, Sagamihara; Katsuya Mizuno, Tokyo, all of Japan

[73] Assignee: Sankin Kogyo Kabushiki Kaisha, Tokyo, Japan

[21] Appl. No.: 548,000

[22] Filed: Nov. 2, 1983

[30] Foreign Application Priority Data

Nov. 5, 1982 [JP] Japan .................................. 57-193526

[51] Int. Cl.³ ................................................ A61C 3/00
[52] U.S. Cl. ....................................................... 433/75
[58] Field of Search ......................... 433/53, 75, 51, 50

[56] References Cited

U.S. PATENT DOCUMENTS

| | | | |
|---|---|---|---|
| 1,910,592 | 5/1933 | Craigo | 433/51 |
| 2,007,884 | 7/1935 | Spiro | 433/51 |
| 2,457,090 | 12/1948 | Ringle et al. | 433/75 |
| 2,616,176 | 11/1952 | Rodin | 433/50 |
| 2,703,453 | 3/1955 | Landis | 433/75 |

FOREIGN PATENT DOCUMENTS 122101 9/1946 Australia ............................... 433/75

*Primary Examiner*—John J. Wilson
*Attorney, Agent, or Firm*—Diller, Ramik & Wight

[57] ABSTRACT

An improved device for measuring an inclination angle of the tapered surface of a plaster die duplicated from the prepared tooth in the field of restorative dentistry is disclosed. The device is used also for scraping operation for the was pattern. It includes a turnable tool holding plate which is turnably held in a slot formed on the lower part of a core so as to turn about a support shaft. A rotary ring with its lower end face cut to a predetermined inclination angle, for instance, 7 degrees is rotatably fitted onto the core in such a manner that the lower inclined face comes in contact with the upper faces of wing-shaped lateral projections of the tool holding plate with a transversely extending shaft disposed therebetween. The transversely extending shaft is inserted through the tool holding plate at the same inclination angle as that of the lower inclined end face of the rotary ring so that its axis intersects with the axis of the support shaft. When a tool on the tool holding plate is to be inclined, a lock ring is loosened and the rotary ring is rotated by an operator's hand. When the rotary ring is rotated by 90 degrees, the tool is caused to incline by 7 degrees. When it is further rotated by 180 degrees, the tool is inclined by 14 degrees. A number of calibration lines are impressed over the peripheral surface of the rotary ring.

9 Claims, 11 Drawing Figures

FIG.5
FIG.6 (a)
FIG.6 (b)
FIG.6 (c)
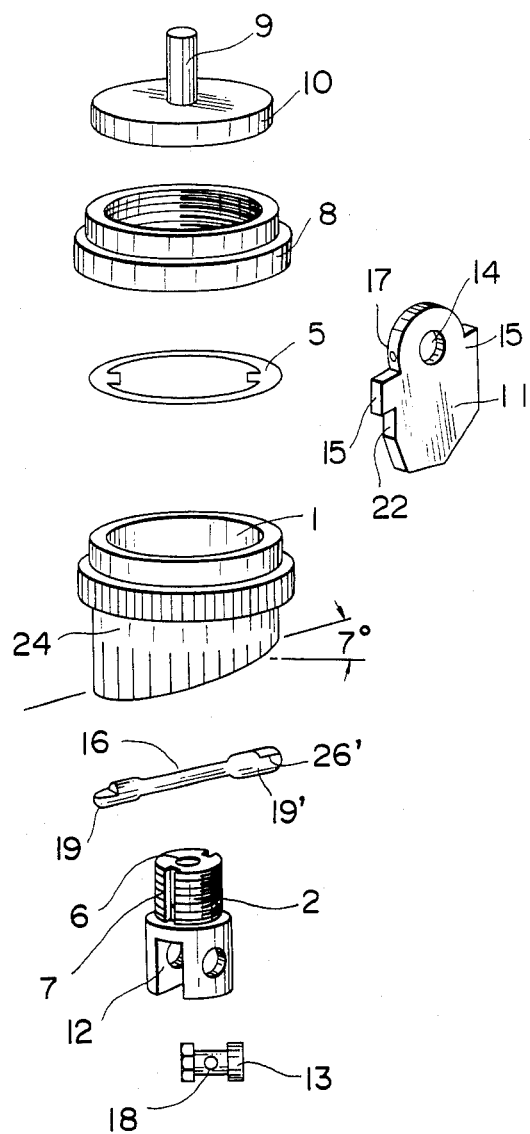
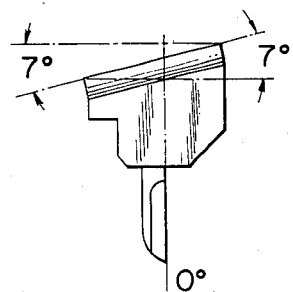
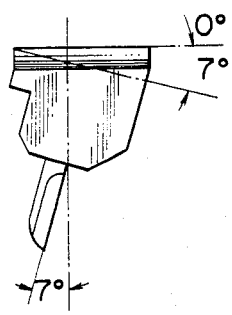
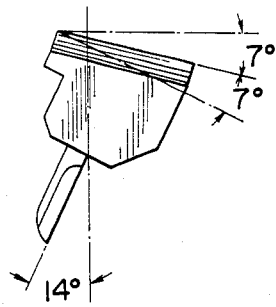

DEVICE FOR MEASURING AND SCRAPING OPERATIONS IN THE FIELD OF PRESTORATIVE DENTISTRY

BACKGROUND OF THE INVENTION

1. Field of the Invention

The present invention relates to a device for measuring and scraping operations in the field of restorative dentistry and more particularly to an improved device for measuring an inclination angle of the tapered surface of a plaster die duplicated from the prepared tooth, said plaster die being mounted on a surveyor utilized in the "conus crown" telescope technology, and scraping a wax patter to be fabricated on the plaster die for partial denture as required.

2. Description of the Prior Art

To remedy drawbacks inherent to the conventional parallel telescope technology in the field of restorative dentistry Dr. Karlheinz Körber in West Germany developed a new technology that is called "conus crown" telescope technology about twenty years ago. This technology has been satisfactorily employed for partial denture and to practice the technology a device for measuring an inclination angle of the tapered surface of a plaster die which forms a part of a partially worked model mounted on a surveyor and scraping it to fabricate a tapered conical crown according to a calculated inclination angle (hereinafter referred to simply as device) was specially designed and fabricated by Dr. Körber. His device was simple in structure but it was found that it had a few problems. One of them is that the device has a long length and thereby it occuplies a wide space on the table of the surveyor. Another problem is that after a tool on the device is inclined due to contact with the tapered surface of a wax pattern, a measured inclination angle is indicated with less accuracy, because an indicator is designed in such a manner that an indicating needle is made integral with the tool and it is actuated by turning about a junction point between the tool and the needle in the lever fashion.

In view of the first mentioned drawback of the conventional device Dr. Körber made an improvement so as to reduce the length of the device. The improvement was made such that an indication needle was oriented in the lateral direction at a right angle relative to the tool but no improvement was achieved with respect to accuracy of measurement. Moreover, it was found that measuring and scraping operations were carried out with much difficulties due to the existence of the transversely extending indicating needle.

SUMMARY OF THE INVENTION

Thus, the present invention has been made with the foregoing background in mind and its object resides in providing an improved device of the above-mentioned type which assures that it is designed and constructed in smaller dimentions and a measured inclination angle can be visually recognized with high accuracy.

Other object of the invention is to provide an improved device of the above-mentioned type which assures that a tool can be firmly locked at any inclination angle.

Another object of the invention is to provide an improved device of the above-mentioned type which requires no specially trained skill.

Still another object of the invention is to provide an improved device of the above-described type which assures that an inclination angle of a tool can be observed from any direction without difficult.

To accomplish the above objects there is proposed in accordance with the present invention a device of the above-mentioned type which comprises in combination a rotary ring of which lower end face is cut to a predetermined inclination angle, said rotary ring having a number of calibration lines impressed over the peripheral surface thereof, a core onto which the rotary ring is rotatably fitted, a tool holding plate inserted into a slot formed on the lower part of said core so as to turn about a support shaft which is fixedly secured to said tool holding plate, the latter having wing-shaped lateral projections each of which upper face extends at the same inclination angle as that of the lower inclined end face of the rotary ring, a tranversely extending shaft inserted through the tool holding plate at the same inclination angle as that of the lower inclined end face of the rotary ring, the axis of said transversely extending shaft intersecting with the axis of the support shaft at a right angle relative to one another, a lock ring for inhibiting rotation of the rotary ring at its lowermost position, resilient means for normally thrusting downward the rotary ring so that the lower inclined end face of the rotary ring comes in contact with both the end parts of the transversely extending shaft, and a cover threadably fitted onto the male thread portion of the core.

In the "conus crown" telescope technology an inclination angle of the tappered surface of a plaster die duplicated from the prepared tooth is generally defined within 14 degrees in the light of hitherto encountered experiences and therefore the inclination angle of the lower inclined end face of the rotary ring is determined to 7 degrees whereby a tool attached to the tool holding plate can be inclined within an extent of 14 degrees by rotating the rotary ring with the lock ring being loosened.

Accordingly, the upper surfaces of the wing-shaped lateral projections of the tool holding plate are inclined at an inclination angle of 7 degrees, whereas the transversely extending shaft is inclined also at an inclination angle of 7 degrees.

The transversely extending shaft is disposed between the lower inclined end face of the rotary ring and the upper faces of the wing-shaped lateral projections of the tool holding plate so that the former comes in surface contact with the latter during rotation of the rotary ring. To achieve the aforesaid surface contact therebetween both the upper faces of the wing-shaped lateral projections of the tool holding plate are formed with a semi-cylindrical recess respectively on which the lower half of the transeversely extending shaft is held so as to cause it to turn by a limited angle as the rotary ring is rotated and moreover both the end parts of the transeversely extending shaft are cut to a flat face so that they are brought in slidable contact with the lower inclined end face of the rotary ring.

In a preferred embodiment of the invention the resilient means for normally thrusting downward the rotary ring is constructed by a combination of a coil spring inserted into a drilled hole on the male thread portion of the core, a ring-shaped washer fitted onto the male thread portion of the core, said ring-shaped washer having a pair of inward projections located diametrically opposite to one another, and an intermediate member bridged between said inward projections of the ring-shaped washer. Thus, resilient force of the coil spring is transmitted to the rotary ring via the intermediate member and the ring-shaped washer.

The calibrations lines indicating zero to 14 degrees are impressed over one half of the peripheral surface of the rotary ring and a reference line to be located in vertical alignment with one of the calibration lines is impressed on the one outermost end face of the transversely extending shaft.

To allow the calibration lines to be observed from any direction the same calibration lines may be impressed over both the halves of the peripheral surface of the rotary ring and reference lines may be impressed on both the outermost end faces of the transversely extending shaft. In this case the calibration lines on both the halves of the perpheral surface of the rotary ring as well as the reference lines on both the outermost end faces of the transversely extending shaft are identified with different colors. Typically, the calibration lines on the one half of the perpheral surface of the rotary ring and the associated reference line are colored with black, whereas the calibration lines on the other half of the same and the associated reference line are colored with red.

Other objects, features and advantages of the invention will become more clearly apparent from reading of the following description which has been prepared in conjunction with the accompanying drawings.

BRIEF DESCRITION OF THE DRAWINGS

The accompanying drawings will be briefly described below.

FIG. 5 is a perspective view of essential components constituting the device, shown in the disassembled state.

FIG. 6(a) is a side view of the tool holding plate with a tool attached thereto, illustrating that it is not inclined.

FIG. 6(b) is a side view of the tool holding plate in FIG. 6(a), illustrating that it is inclined by 7 degrees.

FIG. 6(c) is a side view of the tool holding plate in FIG. 6(a), illustrating that it is inclined by 14 degrees.

DETAILED DESCRIPTION OF THE EMBODIMENT

Figure 1:
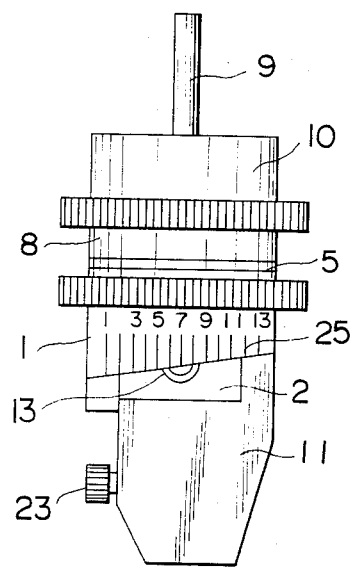
FIG. 1 is a side view of a device in accordance with a preferred embodiment of the invention with a tool removed therefrom.

Now, the present invention will be described in a greater detail hereunder with reference to the accompanying drawings which illustrate a preferred embodiment of the invention.

As is best seen from FIG. 5, a device of the invention essentially comprises a rotary ring 1 of which lower end face is cut to a predetermined inclination angle, that is, 7 degrees in the illustrated embodiment, a core 2 onto which said rotary ring 1 is rotatably fitted, a tool holding plate 11 inserted into a slot 12 formed on the lower part of the core 2 so as to turn about a support shaft 13 which is fixedly fitted to said tool holding plate 11, the latter having wing-shaped lateral projection of which upper face extending at the same inclination angle as that of the lower inclined end face of the rotary ring 1 and having a semi-cylindrical recess formed thereon, a transversely extending shaft 16 inserted through holes 17 at the upper part of the tool holding plate 11 along the semi-cylindrical recesses on the upper faces of the wing-shaped lateral projections, a ring-shaped washer 5 having a pair of inward projections located diametrically opposite to one another, said projections being fitted into grooves 7 vertically extending across the male thread portion of the core 2, a lock ring 8 for inhibiting rotation of the rotary ring 1 at its lowermost end position and a cover 10 threadably fitted onto the male thread portion of the core 2.

Figure 8:
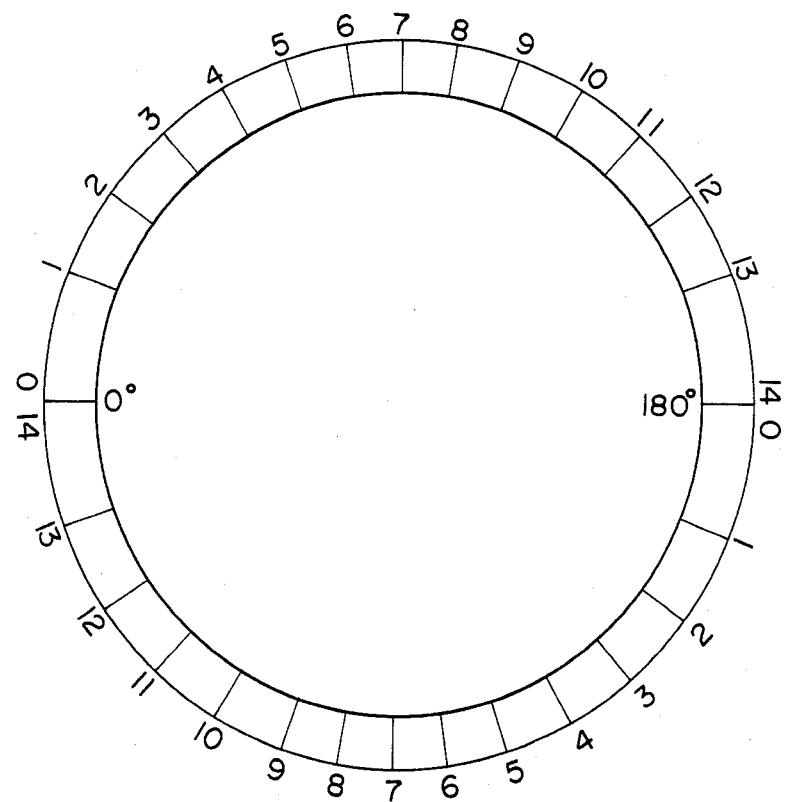
FIG. 8 is a schematic view illustrating how calibration is made over the peripheral surface of the rotary ring.

To assure that the rotary ring 1 and the lock ring 8 are easily rotated by an operator's hand they have a knurled portion respectively and the rotary ring 1 has a number of calibration lines 25 impressed along the whole peripheral surface 24 thereof so as to indicate how a tool 20 is inclined. In the illustrated embodiment a calibration line indicating zero degree is located at the lefthand side of the peripheral surface 24 as seen in FIG. 1 and a calibration line indicating 14 degrees is located at the righthand side of the same. As is apparent from FIG. 8, an angular distance between the adjacent calibration lines is not equal along the whole peripheral surface 24. It becomes largest between zero degree and one degree as well as 13 degrees and 14 degrees and it gradually decreases toward the middle part between zero degree and 14 degrees.

A coil spring 3 is received in a smaller bore 6 on the male thread portion of the core 2 so that its resillient force is transmitted to the rotary ring 1 via a key-shaped intermediate member 4 and a washer 5 so as to allow the rotary ring 1 to be normally thrusted downward against flat faces on both the end parts 19 and 19' of the transversely extending shaft 16. To slidably receive the key-shaped intermediate member 4 a slot 7 is formed through the male thread portion of the core 2 in the transverse direction at the lower end part of the vertically extending grooves 7.

Figure 4:
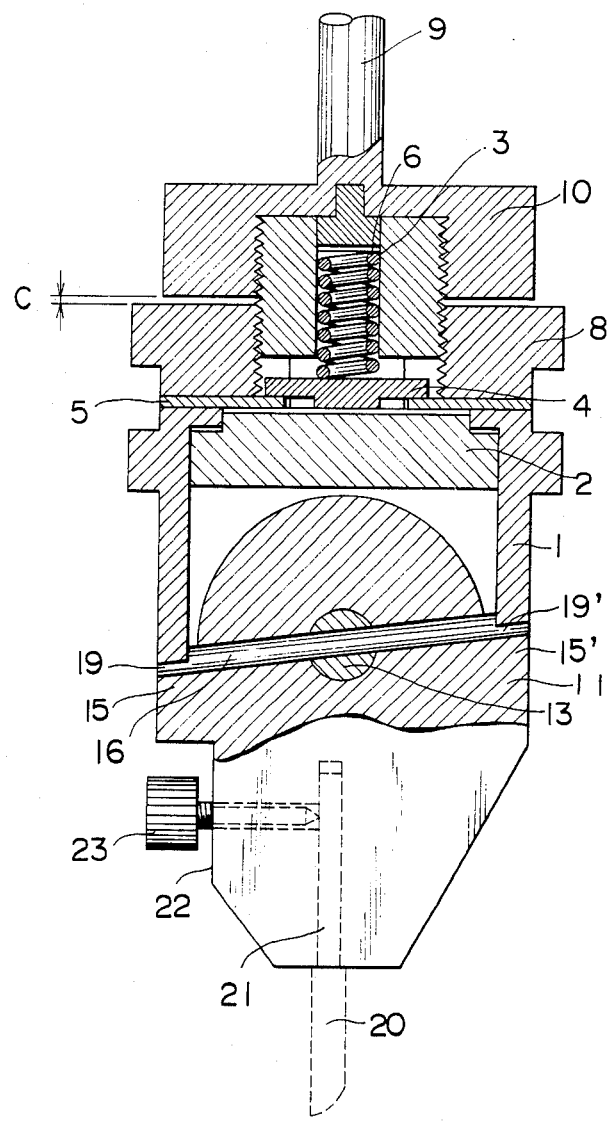
FIG. 4 is a vertical sectional view of the device in FIG. 1, shown in an enlarged scale.
Figure 7:
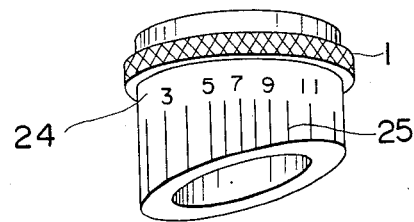
FIG. 7 is a perspective view of the rotary ring of which lower end face is cut to 7 degrees, particularly illustrating how calibration lines are impressed on the peripheral surface of the rotary ring.

As is apparent from FIG. 4, there is existent a very close clearance C between the cover 10 and the lock ring 8 when the latter is turned to the lowermost position to inhibit the rotary ring 1 from further rotation. As required, the lock ring 8 is turned in the opposite direction so as to be released from the locked state.

Since the laterally extending shaft 16 extends through the holes 17 on the tool holding plate 11 and the hole 18 on the support shaft 13 along the semi-cylindrical recess on the upper end faces of the wing-shaped lateral projections, it is inclined at the same inclination angle as that of the lower inclined face of the rotary ring 1 and its axis intersects with the axis of the support shaft 13 at a right angle relative to one another which is fixedly fitted to the tool holding plate 11.

Both the end parts 19 and 19' of the transversely extending shaft 16 are cut to a flat face which is normally brought in slidable contact the lower inclined face of the rotary ring 1 while the latter is rotated. Thus, due to the slidable contact between the flat faces of the end parts 19 and 19' of the transversely extending shaft 16 and the lower inclined face of the rotary ring 1 the transvesely extending shaft 16 is caused to rotate within a certain angular extent in the semi-cylindrical recesses on the upper faces of the wing-shaped lateral projections of the tool holding plate 11 as the rotary ring 1 is rotated. Provided that there is existent no transversely extending shaft on the upper faces of the wing-shaped lateral projections of the tool holding plate 11, it will result that the lower inclined end face of the rotary ring 1 comes in direct contact with the upper surfaces of the wing-shaped projections of the tool holding plate 11 whereby they wears quickly because of the fact that line contact is achieved therebetween during rotation of the rotary ring 1. To prevent occurance of line contact as described above there is provided the transversely extending shaft 16 between the rotary ring 1 and the tool holding plate 11, said transversely extending shaft 16 being caused to rotate within an appreciable extent of angle on the semi-cylindrical recesses on the upper faces of the wing-shaped projections of the tool holding plate 11.

In FIG. 4 reference numeral 22 designate a cutout formed at the lower part of the lefthand wing-shaped laterla projection 15 so that a set screw 23 for firmly holding a tool 20 on the tool holding plate 11 is accomodated in said cutout 22. Thus, the device can be handled without any hindrance due to the existence of projection such as set screw or the like means.

Next, operation of the device will be described below.

Figure 9:
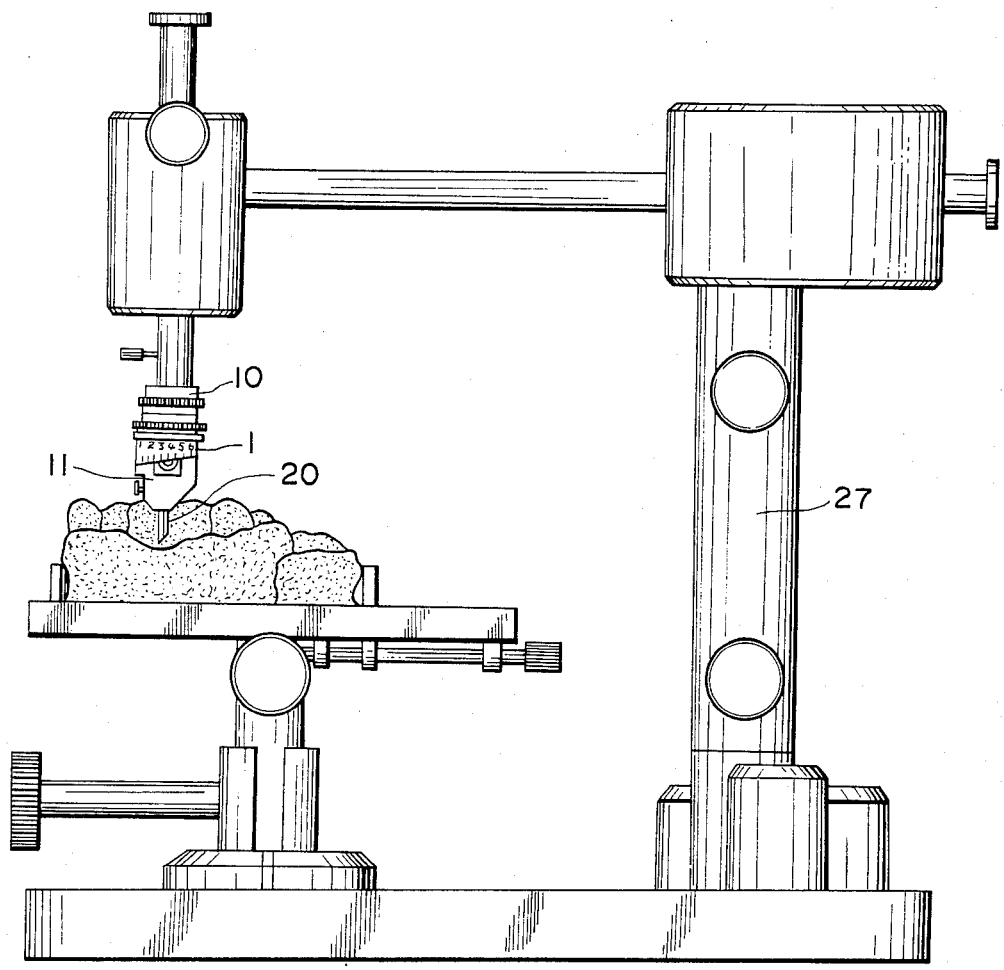
FIG. 9 is a side view of a surveyor with the device attached thereto, illustrating that the device is operated for a partial denture to be designed on a partially worked plaster model mounted on a table.

A tool 20 is first inserted into a drilled hole 21 on the tool holding plate 11 and then it is firmly held thereon by tightening a set screw 23. The thus prepared device is attached to a surveyor 27 by inserting a shank 9 on the cover 10 into a collet of the surveyor 27 (see FIG. 9). The device is displaced to the position located just in front of a plaster die to be inspected by actuating the parallel actuating mechanism of the surveyor 27.

Prior to initiating measuring operation the locking ring 8 is loosened so that the rotary ring 1 is easily rotated by an operator's hand. While this state is maintained, the tool 20 is brought in contact against the tapered surface of the plaster die. After it is confirmed that the tool 20 assumes the position located in paralle to the tapered surface, the existing inclination angle of the tapered surface of the wax pattern relative to a vertical plane can be measured by reading the numeral on the calibration line which is located in vertical alignment with the reference line 26 marked on the outermost end face of the transversely extending shaft 16.

Figure 2:
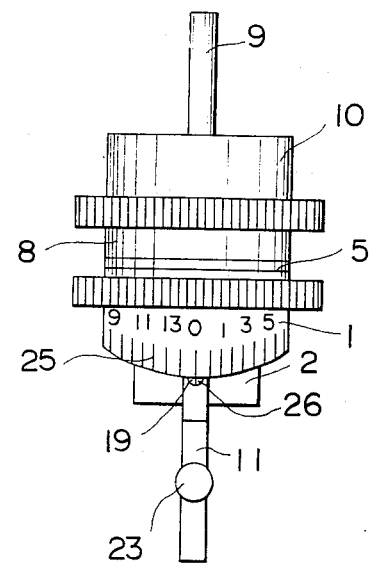
FIG. 2 is a front view of the device in FIG. 1.
Figure 3:
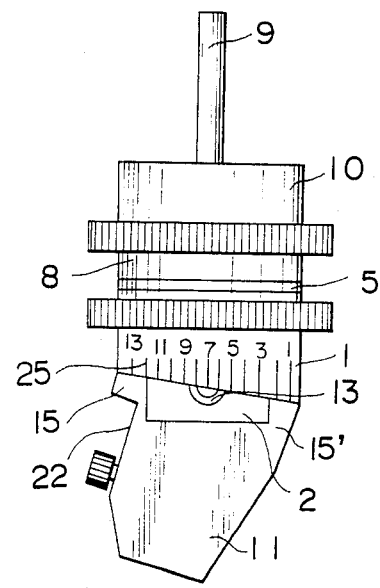
FIG. 3 is a side view of the device, particularly illustrating that a rotary ring is rotated by 180 degrees and thereby a tool holding plate is inclined by 14 degrees.

In this connection it should be noted that calibration is made for the device in such a manner that when the tool 20 assumes the vertical posture without any inclination as illustrated in FIGS. 4 and 6(a), the calibration line indicating zero degree is located in vertical alignment with the reference line 26 as is best seen from FIG. 2, when the rotary ring 1 is rotated by 90 degrees and the tool 20 is inclined by 7 degrees as illustrated in FIG. 6(b), the calibration line indicating 7 degrees is located in vertical alignment with the reference line 26 and when the rotary ring 1 is rotated by 180 degrees as illustrated in FIG. 3 and the tool 20 is inclined by 14 degrees as illustrated 6(c), the calibration line indicating 14 degrees is located in vertical alignment with the reference line 26.

After the existing inclination angle of the tapered surface of the plaster die is measured, scraping operation is carried out. The tool 20 is rearranged by manual operation such that it is inclined to a required inclination angle which is calculated in accordance with the Dr. Körber's "conus crown" theory and its cutting edge is oriented toward the tapered surface of the wax pattern. After completion of rearrangement the lock ring 8 is turned in the direction of locking. The whole device with the tool 20 inclined to the predetermined inclination angle is displaced toward the wax pattern by operating the parallel actuating mechanism of the surveyor and scraping operation is then carried out by manually handling the device.

As described above, any inclination of the tool 20 in the range of 0 to 14 degrees can be obtained by rotating the rotary ring 1 at the largest by 180 degrees corresponding to rotation of the latter by a half turn. Accordingly, calibration is required only over the half of the peripheral surface 24 of the rotary ring 1 but in the illustrated embodiment of the invention the same calibration is made over the other half of the peripheral surface 24 of the rotary ring 1 as is apparent from FIGS. 2 and 8 in order to assure that the existing inclination angle can be read from any direction. To identify the direction of observation it is convenient that the calibration lines on the one half of the peripheral surface 24 of the rotary ring 1 are colored with black and those on the other half of the same are colored with red.

The red colored reference line 26' on the righthand outermost end face of the transversely extending shaft 16 as seen in the drawing is adapted to be located in vertical alignment with the red colored calibration lines on the other half of the peripheral surface 24 of the rotary ring 1 so that the existing inclination angle of the tool can be easily recognized from the opposite direction.

While the invention has been described above merely with respect to a single preferred embodiment, it should of cource be understood that it should not be limited only to this but various changes or modifications may be made in a suitable manner without any departure from the spirit and scope of the invention.

What is claimed is:

1. In a device for measuring an inclination angle of the tapered surface of a plaster die duplicated from the prepared tooth, said plaster die being mounted on a surveyor utilized in the "conus crown" telescope technology, and scraping a wax pattern on the plaster die so as to fabricate a tapered conical crown with an adequate inclination angle to retain a partial denture, the improvement consisting in that said device essentially comprises;

a rotary ring having a lower end face which is cut to a predetermined inclination angle, said rotary ring having a number of calibration lines impressed over the peripheral surface thereof, core means onto which said rotary ring is rotatably fitted, tool holding means inserted into the core means so as to turn about a support shaft, said tool holding means having a pair of lateral projections each of which upper face extends at the same inclination angle as that of the lower inclined end face of the rotary ring, a lock ring for inhibiting rotation of the rotary ring when the tool holding means is to be fixedly held, resilient means for normally thrusting downward the rotary ring so that the lower inclined end face of the rotary ring comes in slidable contact with both the upper faces of the lateral projections of the tool holding means, and fitting means firmly fitting the device to the surveyor, said fitting means serving also as a cover for the device.

2. A device as defined in claim 1, wherein a transversely extending shaft is disposed between the lower inclined end face of the rotary ring and upper faces of the lateral projections of the tool holding means, the axis of said transversely extending shaft intersecting with the axis of the support shaft at a right angle relative to one another.

3. A device as defined in claim 1, where the inclination angle of the lower inclined end face of the rotary ring is selectively determined to 7 degree so that a tool attached to the tool holding means is inclinable within an extent of 14 degrees by rotating the rotary ring with the lock ring loosened.

4. A device as defined in any one of claims 1 to 3, wherein the upper faces of the lateral projections of the tool holding means are inclined at an inclination angle of 7 degrees and the traversely extending shaft is inclined also at an inclination angle of 7 degrees.

5. A device as defined in claim 4, wherein both the upper faces of the lateral projections of the tool holding means are formed with a semi cylindrical recess respectively on which the lower half of the transversely extending shaft is turnably held and both the end parts of the transversely extending shaft are out to a flat face with which the lower inclined end face of the rotary ring is brought in slidable contact so that the transversely extending shaft turns within a certain angle as the rotary ring is rotated.

6. A device as defined in claim 1, wherein the resilient means for normally thrusting downward the rotary ring comprises a coil spring inserted into a hole on the male thread portion of the core means, a ring-shaped washer of fitted onto the male thread portion of the core means, said ring-shaped washer having a pair of inward projections located diametrically opposite to one another, and an intermediate member bridged between said inward projections of the ring-shaped washer.

7. A device as defined in claim 1, wherein the calibration lines are impressed over one half of the peripheral surface of the rotary ring and a reference line to be located in vertical alignment with one of the calibration lines is impressed on the one outermost end face of the transversely extending shaft.

8. A device as defined in claim 1, wherein the calibration lines are impressed over both halves of the peripheral surface of the rotary ring and reference lines to be located in vertical alignment with one of the calibration lines are impressed on both the outermost end faces of the transversely extending shaft.

9. A device as defined in claim 7, wherein the calibration lines over both the halves of the peripheral surface of the rotary ring as well as the associated reference lines on both the outermost end faces of the transversely extending shaft are identified with different colors.

* * * * *